United States Patent [19]  [11] 4,297,500
Finke et al.  [45] Oct. 27, 1981

[54] CONVERSION OF LOW-BOILING CONSTITUENTS FROM ALKYL-CHLOROSILANE SYNTHESIS

[75] Inventors: Ulrich Finke, Ettlingen; Hans-Heinrich Moretto, Cologne, both of Fed. Rep. of Germany

[73] Assignee: Bayer Aktiengesellschaft, Leverkusen, Fed. Rep. of Germany

[21] Appl. No.: 209,932

[22] Filed: Nov. 24, 1980

[30] Foreign Application Priority Data

Dec. 14, 1979 [DE] Fed. Rep. of Germany ....... 2950402

[51] Int. Cl.$^3$ ............................................... C07F 7/08
[52] U.S. Cl. ..................................... 556/466; 556/478
[58] Field of Search ................................. 556/466, 478

[56] References Cited

U.S. PATENT DOCUMENTS 2,500,652  3/1950  Barry et al. ......................... 556/466
2,628,243  2/1953  Barry et al. ......................... 556/466
2,752,379  6/1956  Wagner et al. ...................... 556/466

*Primary Examiner*—Paul F. Shaver
*Attorney, Agent, or Firm*—Sprung, Felfe, Horn, Lynch & Kramer

[57] ABSTRACT

A process for converting the low-boiling constituents formed in the preparation of methylchlorosilane to the Müller-Rochow process and which consist essentially of tetramethylsilane, dimethylmonochlorosilane and 2-methylbut-2-ene into a product mixture consisting essentially of trimethylchlorosilane, dimethylchlorosilane and $C_{2-20}$ alkyldimethylchlorosilanes or $C_{6-10}$-aryldimethylchlorosilanes, comprising contacting the low-boiling product mixture with $AlCl_3$, $AlOCl$ and/or $AlBr_3$, together with hydrogen chloride, in the liquid phase at about 40° to +25° C. The mixture prior to conversion may be contacted with HCl and either $ZnCl_2$ or active charcoal and/or an olefin may be added thereto.

4 Claims, No Drawings

CONVERSION OF LOW-BOILING CONSTITUENTS FROM ALKYL-CHLOROSILANE SYNTHESIS

The present invention relates to a process for converting low-boiling constituents from the synthesis of alkylchlorosilanes into more valuable products by catalytic treatment in the liquid phase at low temperatures.

The preparation of methylchlorosilanes by direct synthesis (Rochow-Müller process) results in the unavoidable formation of a considerable proportion of low-boiling products with a boiling point <40° C. (760 mm Hg), such as, for example, tetramethylsilane (TMS) and dimethylmonochlorosilane, in addition to the desired products methyltrichlorosilane, dimethyldichlorosilane and trimethylchlorosilane. TMS is of no further importance for silicone chemistry since it carries no functional group on the silicon. TMS has hitherto therefore been destroyed. In contrast to TMS, dimethylmonochlorosilane has functional groups on the silicon and is thus capable of further reactions, but preparation of this compound in a pure form from the product mixture presents considerable difficulties because of the presence of 2-methyl-but-2-ene, which has virtually the same boiling point.

It is thus an object of the invention to convert the product mixture obtained into compounds useful in silicone chemistry and hence of increasing the yield of valuable chlorosilanes without first having to carry out expensive separation processes.

It has been found, surprisingly, that the conversion of the compounds contained in the product mixture, such as tetramethylsilane, dimethylmonochlorosilane and 2-methylbut-2-ene into the compounds which are important in silicone chemistry, that is to say trimethylchlorosilane, dimethyldichlorosilane and alkyldimethylchlorosilanes, can be effected in a simple manner by reacting the product mixture with $AlCl_3$, $AlOCl$ and/or $AlBr_3$ and HCl in the liquid phase.

The present invention therefore relates to a process for converting the low-boiling constituents which are formed in the preparation of methylchlorosilane (Müller-Rochow process) and which essentially consist of tetramethylsilane, dimethylmonochlorosilane and 2-methylbut-2-ene into product mixtures essentially consisting of trimethylchlorosilane, dimethylchlorosilane and alkyldimethylchlorosilanes (alkyl radical with 2 to 20 C atoms) or aryldimethylchlorosilanes (aryl radical with 6 to 10 C atoms), which is characterized in that the low-boiling product mixture is brought into contact with $AlCl_3$, $AlOCl$ and/or $AlBr_3$, together with hydrogen chloride, in the liquid phase at $-40°$ C. to $+25°$ C.

In addition to the substances already mentioned, which essentially form the mixture, the starting mixture can also contain methyl chloride, ethyl chloride, 2-methylbutane, silicon tetrachloride, silicochloroform and 2-methylbut-2-ene. However, relatively small amounts of these products are present. The end products can therefore also contain, for example, the following compounds: hydrogen, methane, ethane and 2-methylbutane.

It is particularly surprising that the reaction of tetramethylsilane with hydrogen chloride and $AlCl_3$, $AlOCl$ or $AlBr_3$ to give trimethylchlorosilane also proceeds at temperatures of $-40°$ C., since this reaction has hitherto been carried out only at relatively high temperatures (compare U.S. Pat. No. 2,802,852 and German Offenlegungsschrift 2,546,919). Furthermore, the use of pure TMS or enriched TMS fractions (containing at least 50 percent by weight) is a precondition of the known processes and is associated with considerable expenditure and appears uneconomical. However, these processes are suitably exclusively for the conversion of tetramethylsilane, of which only relatively low concentrations are frequently found, in addition to dimethylmonochlorosilane, 2-methylbut-2-ene and other compounds, in the product mixture obtained. The reaction conditions chosen in the processes mentioned are unsuitable for realizing the conversions described here.

The conversion of $Me_2SiHCl$ ($Me=CH_3-$) into dimethyldichlorosilane by means of $AlCl_3/HCl$ or $AlCl_3/CH_3Cl$ or $C_2H_5Cl$ which is likewise effected according to the invention is also surprising since disproportionation of Me HSiCl in the presence of $AlCl_3$ into $Me_2SiH_2$ and $Me_2SiCl_2$ was to be expected according to MacDiarmid—Organometallic Compounds of the Group IV Elements, volume 2, page 238.

A further advantage of the process according to the invention is the possibility of producing alkyl- or aryl-dimethylmonochlorosilanes (alkyl=$C_nH_{2n+1}$ in which n=2-20), in addition to trimethylchlorosilane and dimethyldichlorosilane.

For this reaction, the product mixture intended for the $AlCl_3/HCl$ reaction is treated with $AlCl_3$ (or $AlOCl$ or $AlBr_3$) at temperatures from $-40°$ to $+25°$ C. In this treatment, in the presence of 2-methylbut-1-ene or 2-methylbut-2-ene the $Me_2HSiCl$ is converted into pentyldimethylmonochlorosilane which is an important product. Such product does not undergo further reaction under the conditions later prevailing so expensive separation thereof can be spared.

If the product unavoidably obtained contains a molar excess of $Me_2SiHCl$ relative to olefin (which is frequently the case), it is advantageous to add olefins for example 2-methylbut-2-ene or any other olefin suitable for this reaction, as required, in order to increase the yield of the desired alkyl- or aryl-dimethylmonochlorosilanes.

Any fraction obtained in the Rochow-Müller process which has a boiling point of less than 40° C. can be employed in the process according to the invention as the product unavoidably obtained. These fractions as a rule contain tetramethylsilane, dimethylmonochlorosilane, 2-methylbut-1-ene and 2-methylbut-2-ene as the main constituents. $CH_3Cl$, ethyl chloride, 2-methylbutane, $SiCl_3H$ and $SiCl_4$ and other compounds are also present as by-products. The composition can vary greatly and depends on the procedure in the Rochow synthesis and on the composition of the catalyst in this process.

The amount of hydrogen chloride employed in the process according to the invention can be determined by analysis of the content of the product mixture which reacts with HCl, that is to say tetramethylsilane, dimethylmonochlorisilane and in certain circumstances 2-methylbut-2-ene. Molar amounts are required in each case. It is advantageous to use a slight excess of hydrogen chloride. The catalyst concentration depends on the desired procedure. In the case of a discontinuous procedure, a catalyst amount of about 0.1 to 1% by weight, relative to the reaction mass, of $AlCl_3$ (or $AlOCl_3$ or $AlBr_3$) is sufficient. In the case of continuous operation, it is advantageous to use relatively high catalyst concentrations in order to achieve high space/time yields.

The temperature at which the process according to the invention is carried out is preferably about −40° C. to +25° C., in particular about −30° C. to +20° C.

The process according to the invention is preferably carried out under the pressure of the surrounding atmosphere. If desired, however, higher or lower pressures can also be applied.

The conversions achieved in the process according to the invention are in general 90–100 mol%, in each case relative to the reactants employed in the smallest amount.

The selectivity can be 90–100% for the conversion of tetramethylsilane into trimethylchlorosilane.

The selectivity for the conversion of Me$_2$SiHCl into dimethyldichlorosilane is between 90 and 98% in the reaction with AlCl$_3$/HCl. The selectivity can be increased to 100% if, according to a particular embodiment of the process according to the invention, the product unavoidably obtained is simply treated with ZnCl/HCl or active charcoal/HCl at temperatures of up to about 40° C. before the reaction with AlCl$_3$ or AlCl$_3$/HCl. No splitting of TMS into trimethylchlorosilane, as described in U.S. Pat. No. 2,802,852, takes place in this case. The process step of treatment with ZnCl$_2$/HCl or active charcoal/HCl furthermore enables Me$_2$SiHCl which is free from 2-methylbut-2-ene to be separated off by distillation, the 2-methylbut-2-ene being converted into amyl chloride, which has a lower volatility. Me$_2$SiHCl can therefore be separated off in a simple manner as required.

The reaction products obtained in the process according to the invention can be distilled in a simple manner together with the methylchlorosilanes obtained in the reaction of silicon with methylchlorosilanes.

The process according to the invention can be carried out with or without solvents, as desired. Examples of suitable solvents are saturated hydrocarbon fractions of which the boiling range does not lie within the boiling range of the product or of a starting component which can be recovered. Low-boiling or high-boiling paraffin oils, for example, can be employed.

GENERAL INSTRUCTIONS

The following reactions are carried out in the absence of oxygen and moisture in a 0.5 l four-necked flask with an internal thermometer, a reflux condenser with a gas outlet, a dropping funnel and a gas inlet tube:

Example 1

100 g of a product which is unavoidably obtained and contains 46% of TMS, 20% of Me$_2$SiHCl. 12% of 2-methylbut-2-ene and 3% SiCl$_3$H, 1% CH$_3$Cl, 13% MeSiCl$_2$H and 5% 2-methylbutane are added dropwise to a mixture of 1 g of AlCl$_3$ in 10 ml of pentane, which is cooled to 0° and continuously saturated with HCl through the gas inlet tube, at a rate such that the temperature does not exceed 10° C. (cooling). The amount of HCl added is 0.75 mol.

Yield: 98% of Me$_3$SiCl, relative to TMS, 96.5% of Me$_2$SiCl$_2$, relative to Me$_2$HSiCL, and 1.5% of

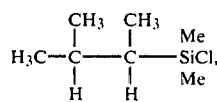

relative to Me$_2$HSiCl.

Other reaction products are, inter alia, hydrogen, methane and 2-methylbutane.

Example 2

The unavoidably obtained product as in Example 1 is added dropwise to a mixture, cooled to 0° C., of 1 g of AlCl$_3$ and 10 g of pentane, without passing in HCl (maximum temperature: +10° C.). When the exothermic reaction has ended, HCl is passed in, while still cooling. The reaction is ended when the reaction mixture takes up no further HCl. Consumption of HCl: ∼0.58 mol.

Yield: 98% of (CH$_3$)$_3$SiCl, relative to TMS, 20% of (CH$_3$)$_2$SiCl$_2$, relative to Me$_2$SiHCl and 98% of (CH$_3$)$_2$Pent SiCl, relative to 2-methylbut-2-ene

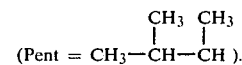

Example 3

5 g of ZnCl$_2$ are added to 100 g of the product unavoidably obtained, and 0.2 mol of HCl is passed in. The reaction temperature should not exceed 40° C. AlCl$_3$ is then added, while adding further HCl and cooling to +10° C. The amount of HCl to be added is about 0.58 mol.

Yield: 98.5% of (CH$_3$)$_3$SiCl, relative to TMS, 98% of (CH$_3$)$_2$SiCl$_2$, relative to Me$_2$HSiCl, and 0% of

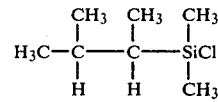

In all the examples, HCl is added at a rate of about 10–15 l/hour.

It will be appreciated that the instant specification and examples are set forth by way of illustration and not limitation, and that various modifications and changes may be made without departing from the spirit and scope of the present invention.

We claim:

1. A process for converting the low-boiling constituents formed in the preparation of methylchlorosilane in the Müller-Rochow process and which consist essentially of tetramethylsilane, dimethylmonochlorosilane and 2-methylbut-2-ene into a product mixture consisting essentially of trimethylchlorosilane, dimethylchlorosilane and C$_{2-20}$ alkyldimethylchlorosilanes or C$_{6-10}$-aryldimethylchlorosilanes, comprising contacting the low-boiling product mixture with AlCl$_3$, AlOCl and/or AlBr$_3$, together with hydrogen chloride, in the liquid phase at about 40° to +25° C.

2. A process according to claim 1, wherein the product mixture is contacted with the AlCl$_3$, AlOCl and/or AlBr$_3$ at about 40° to +25° C. in the liquid phase and the HCl is then added.

3. A process according to claim 1, wherein a compound with a C═C double bond is added to the product mixture before the conversion.

4. A process according to claim 1, wherein the product mixture is contacted with HCl and at least one of ZnCl$_2$ and active charcoal at a temperature up to about +40° C. before conversion.

* * * * *